(12) United States Patent
Westmeyer et al.

(10) Patent No.: US 6,777,569 B1
(45) Date of Patent: Aug. 17, 2004

(54) PROCESS FOR THE MANUFACTURE OF BLOCKED MERCAPTOSILANES

(75) Inventors: Mark D. Westmeyer, Marietta, OH (US); Russell Burton, Marietta, OH (US); Tiberiu L. Simandan, Marietta, OH (US)

(73) Assignee: General Electric Company, Pittsfield, MA (US)

(*) Notice: Subject to any disclaimer, the term of this patent is extended or adjusted under 35 U.S.C. 154(b) by 100 days.

(21) Appl. No.: 10/378,184

(22) Filed: Mar. 3, 2003

(51) Int. Cl.$^7$ .................................................. C07F 7/04
(52) U.S. Cl. ........................................ 556/429; 556/427
(58) Field of Search ................................. 556/429, 427

(56) References Cited

U.S. PATENT DOCUMENTS

| | | |
|---|---|---|
| 5,489,701 A | 2/1996 | Childress et al. |
| 5,596,116 A | 1/1997 | Childress et al. |
| 6,229,036 B1 | 5/2001 | Batz-Sohn et al. |
| 6,294,683 B1 | 9/2001 | Johnson et al. |
| 6,384,255 B1 | 5/2002 | Backer et al. |
| 6,414,061 B1 | 7/2002 | Cruse et al. |

FOREIGN PATENT DOCUMENTS

| | | |
|---|---|---|
| DE | 3803243 | 9/1988 |
| EP | 0773224 | 5/1997 |

OTHER PUBLICATIONS

Luginsland, H. D., et al., Reactivity of the Sulfur Chains ..., KGK Kautschuk Gummikunstsoffe 53 Nr. Jan.–Feb. 2000, p. 10–.
Miller, C.D. et al., Investigation of 1, 3–Diaminopropanol– 2 ..., vol. 37, No. 1, Jan. 1965, pp. 165–166, J. Analytical.
Sato et al., New Birch Type Reduction ..., Bull Chem Soc., Japan 60, 773–774 (1987).
Yamada et al., Direct Preparation of Anhydrous Sodium ... The Chem Soc. of Japan, Chem Letters, 2002, Jan. 7, 2002, p. 454.
Yu et al., Reductive Desulfurization ... Dept. of Chem., Iowa State University, Feb. 25, 1998, pp. 79–82.
Product Brochure for Crompton Corporation, 2002, 8 pages.
Arnold et al., The Action of Lithium ..., J. Am. Chem. Soc. 1950, 72, 731–733.
Brown et al., Selective Reduction of Disulfides ..., Richard B. Wetherill Laboratory, Purdue Univ., Communications, pp. 498–500.
Cha et al., Reduction of Disulfides ..., Bull. Korean Chem., Soc. vol. 13, No. 6, 1992, pp. 702–704.
Klayman et al., Use of Sodium Borohydride ..., Int. J. of Sulfur Chemistry 1973, 8(1), 53–4 English Abstract.

*Primary Examiner*—Samuel Barts

(57) ABSTRACT

A process for the manufacture of a blocked mercaptosilane comprising:

reacting at least one polysulfane-containing organosilicon compound of the general formula:

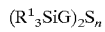

$(R^1_3SiG)_2S_n$ (a) in which each $R^1$ is independently methoxy, ethoxy or alkyl of from 1 to about 6 carbon atoms, provided, that at least one $R^1$ group is methoxy or ethoxy, G is an alkylene group of from 1 to about 12 carbon atoms and n is from 2 to about 8, with at least one alkali metal, alkaline earth metal or a basic derivative of an alkali metal or alkaline earth metal to provide the corresponding metal salt of the polysulfane-containing organosilicon compound and;
(b) reacting the metal salt of the polysulfane-containing organosilicon compound with an acyl halide or carbonyl dihalide to provide a blocked mercaptosilane.

14 Claims, No Drawings

PROCESS FOR THE MANUFACTURE OF BLOCKED MERCAPTOSILANES

BACKGROUND OF THE INVENTION

1. Field of the Invention

This invention relates to a process for the preparation of a blocked mercaptosilane, from a metal salt of a polysulfane-containing organosilicon compound and an acyl halide or carbonyl dihalide, wherein the metal salt of the polysulfane-containing organosilicon compound is formed by reacting a polysulfane-containing organosilicon and an alkali metal, alkaline earth metal or a strong base derived from an alkali metal or alkaline earth metal. This invention also relates to the use of said blocked mercaptosilane as a coupling agent in rubber mixtures.

2. Description of Related Art

Sulfur-containing organosilicon compounds are useful as essential components in the production of silica-filled tires. A silica-filled tire provides for enhanced performance in automotive applications, specifically, improved abrasion resistance, rolling resistance and wet-skidding properties. There are a broad range of sulfur-containing organosilicon compounds that are used as coupling agents in silica-filled tires. Mercapto-containing organosilicon compounds offer superior coupling at reduced loading, however, their chemical reactivity with organic polymers results in unacceptably high viscosities during processing and premature curing. Blocked mercaptosilanes have been shown to maintain the benefits of mercapto-containing organosilicon compounds without displaying the aforenoted problems. The blocked mercapto-containing organosilicon compounds, in particular, thiocarboxylic-containing silicon compounds, can be prepared by reacting a mercapto-containing silicon compound with an acid halide. The byproduct of this reaction, hydrogen chloride, reacts with the organosilicon compound degrading the desired product, and generating chlorosilanes. These reactions with hydrogen chloride are very fast and cannot be prevented by conventional mechanical means, i.e., temperature or pressure, due to the high solubility of the hydrogen chloride in the product. Neutralization of the above noted chlorosilanes can be done using a base such as sodium alkoxide, or propylene oxide, but degradation of the product and/or an undesirable mixture is obtained making this approach undesirable.

Another process used previously, is to neutralize the hydrogen chloride, in situ, using an acid acceptor, i.e., tertiary amine, see U.S. Provisional Patent Application No. 60/423,577 filed Nov. 4, 2002; but this requires a stoichiometric amount of the amine that reduces batch yield and affords a large amount of an undesirable salt that must subsequently be removed, see U.S. Pat. No. 6,229,036. As is already known, tertiary amine salts are difficult to remove due to their solubility, and conventional filtration methods are mechanically intensive and often lead to poor yields. Furthermore, further processing of the filter cake adds additional costs, such as the disposing of the tertiary amine and the hydrogen chloride salt in itself, which poses significant environmental issues.

As has been shown, the reaction of a metal salt of a mercapto-containing organosilicon compound and an acid halide generates the desired blocked mercaptosilane and a metal halide salt, see U.S. Pat. No. 6,414,061 the contents of which are incorporated herein by reference; but in addition to the previously mentioned difficulties, mercapto-containing organosilicon compounds are expensive making their widespread use prohibitive. Therefore, there is an interest in developing a blocked mercaptosilane using a process that is inexpensive and does not provide for the chemical and environmental concerns noted above. There are a number of known methods to cleave a sulfur-sulfur bond, i.e., the use of bases such as amines, phosphines, metal cyanides, metal hydrides and alkali metals, however, phosphines and metal hydrides are expensive and metal cyanides offer a host of safety concerns.

SUMMARY OF THE INVENTION

Polysulfane-containing silicon compounds are inexpensive and widely available, in addition to their affordability, the metal halide byproduct does not react with the product blocked mercaptosilane nor do polysulfane-containing silicon compounds have the environmental concerns of a tertiary amine halide salt. Alkali metals are both safe and inexpensive. The reaction of an alkali metal with a polysulfane-containing organosilicon compound to generate the metal salt of the polysulfane-containing organosilicon compound, affords the desired acid acceptor, in situ, that can be used to produce the desired blocked mercaptosilane compound and a metal halide salt.

Additionally, the use of an aqueous wash of the product thereby minimizes the aforementioned costs and difficulties of removing the metal salt. Removing the metal halide salt by means of either filtration or by use of a centrifuge requires intensive mechanical unit operations and capital investment, whereas an aqueous wash requires neither but results in a two-phase system where one phase contains the blocked mercaptosilane and the second phase contains an aqueous solution of the metal halide. The primary hazard with this method is the potential for hydrolysis of the blocked mercaptosilane and for organofunctional silanes. However, through the presence of metal halide the ionic character of the aqueous phase is increased and thereby minimizes any hydrolysis reaction, see U.S. Pat. No. 6,294,683.

It is an object of the invention to provide a process for preparing a blocked mercaptosilane for use as a coupling agent, which process minimizes the production of byproducts that react with the blocked mercaptosilane, does not require neutralization or filtering and is commercially affordable.

In keeping with this and other objects of the invention there is provided a process for the manufacture of a blocked mercaptosilane comprising:

(a) reacting at least one polysulfane-containing organosilicon compound of the general formula:

in which each $R^1$ is independently methoxy, ethoxy or alkyl of from 1 to about 6 carbon atoms, provided, that at least one $R^1$ group is methoxy or ethoxy, G is an alkylene group of from 1 to about 12 carbon atoms and n is from 2 to about 8, with at least one alkali metal, alkaline earth metal or a basic derivative of an alkali metal or alkaline earth metal to provide the corresponding metal salt of the polysulfane-containing organosilicon compound and;

(b) reacting the metal salt of the polysulfane-containing organosilicon compound with an acyl halide or carbonyl dihalide to provide a blocked mercaptosilane.

In contrast to the process described in aforementioned U.S. Pat. No. 6,414,061 the process of this invention makes it possible to produce a blocked mercaptosilane from readily available polysulfane-containing organosilicon compounds. This results in a high purity blocked mercaptosilane that does not require neutralization or filtering to remove the byproduct metal halide that is formed upon reaction of the metal salt of the polysulfane-containing organosilicon compound with the acyl halide or carbonyl dihalide.

A further object of this invention is to provide a process that involves the use of an aqueous wash of the final product solution, which unlike the distillation step required in aforementioned U.S. Pat. No. 6,414,061, is a more expedient and efficient way to separate the product blocked mercaptosilane from the metal halide byproduct.

DESCRIPTION OF THE PREFERRED EMBODIMENTS

In the process of this invention, a polysulfane-containing organosilicon compound of the formula $(R^1_3SiG)_2S_n$ in which $R^1$, G and n have the aforestated meanings, and an alkali metal, alkaline earth metal or a strong base derived from the alkali metal or alkaline earth metal, can be considered to react to form a metal salt of the polysulfane-containing organosilicon compound in accordance with the reaction (illustrated for an alkali metal such as sodium):

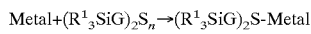
Metal+$(R^1_3SiG)_2S_n$→$(R^1_3SiG)_2$S-Metal

The metal salt of the polysulfane-containing organosilicon compound and a reactive halide such as an acyl halide or carbonyl dihalide, e.g., of the formula $R^2C(O)X$ in which $R^2$ and X have the aforestated meanings, can then be considered to react to form the product blocked mercaptosilane and a metal halide byproduct in accordance with the reaction:

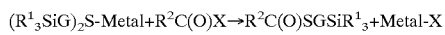
$(R^1_3SiG)_2$S-Metal+$R^2C(O)X$→$R^2C(O)SGSiR^1_3$+Metal-X

Useful polysulfane-containing organosilicon compounds include, for example, bis[(triethoxysilyl)propyl]polysulfane, bis[(methyldiethoxysilyl)propyl]polysulfane, bis[(triethoxysilyl)isobutyl]polysulfane, bis[(methyldiethoxysilyl)isobutyl]polysulfane, bis[(trimethoxysilyl)propyl]polysulfane, bis[(methyldimethoxysilyl)propyl]polysulfane, bis[(trimethoxysilyl)isobutyl]polysulfane, and bis[(methyldimethoxysilyl)isobutyl]polysulfane.

The polysulfane-containing organosilicon compound is reacted with an alkali metal, alkaline earth metal or a strong base derived from an alkali metal or alkaline earth metal. Useful alkali metals, alkaline earth metals and basic metal derivatives include, for example, lithium, sodium, potassium, magnesium, calcium, lithium hydride, sodium hydride, potassium hydride, magnesium hydride, calcium hydride, sodium methoxide, sodium ethoxide, potassium methoxide, potassium ethoxide, and mixtures thereof.

The resulting polysulfane-containing organosilicon compound metal salt is combined with an acyl halide or carbonyl dihalide, e.g., of the general formula $R^2C(O)X$ supra in which $R^2$ is halogen or alkyl, alkenyl, aryl, alkaryl or aralkyl of up to about 18 carbon atoms and X is halogen, to produce a blocked mercaptosilane. Useful acyl halides include acetyl chloride, propanoyl chloride, butanoyl chloride, pentanoyl chloride, hexanoyl chloride, heptanoyl chloride, octanoyl chloride, 2-ethylhexanoyl chloride, lauroyl chloride, oleoyl chloride, octyl chloroformate, adipoyl chloride, phenylacetyl chloride, benzoyl chloride, terephthaloyl chloride, and phenyl chloroformate. Useful carbonyl dihalides include carbonyl dichloride (phosgene), diphosgene, triphosgene, thiophosgene, and oxalyl chloride.

The blocked mercaptosilane product obtained by the foregoing process conforms to the general formula $R^2C(O)SGSiR^1_3$ wherein, $R^1$, $R^2$, and G have the aforesaid meanings. Specific blocked mercaptosilanes include, for example, 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate; 3-triethoxysilyl-1-propyl thiopalmitate; 3-triethoxysilyl-1-propyl thiooctanoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; and 2-methyldiacetoxysilyl-1-ethyl thioacetate.

The reaction of the polysulfane-containing organosilicon compound with alkali metal, alkaline earth metal, or basic derivatives of alkali metal or alkaline earth metal is carried out in mole equivalents of from about 1:1 to about 1:10, and preferably from about 1:2.0 to about 1:2.5. The reaction of the polysulfane-containing organosilicon compound metal salt with acyl halide can be carried out in the range of 1.25:1 to about 1:1 or with a carbonyl dihalide in the range of from about 2.25:1 to about 2:1 mole equivalents.

The reaction between the polysulfane-containing organosilicon compound and the alkali metal, alkaline earth metal or basic metal derivative is conducted at a range of from about ambient temperature to about the melting temperature of the metal or metal derivative used. It is preferably conducted at a temperature wherein the metal used is in a liquid state to increase its surface area such as, for example, from about 25° to about 150° C. and preferably in the range of from about 80° to about 120° C. The subsequent reaction of the metal salt of the polysulfane-containing organosilicon compound and acyl halide or carbonyl dihalide can be carried out at a temperature of from about ambient temperature to about the boiling point of the solvent used; and preferably the temperature is from about 10° to about 50° C. The aqueous wash of the product blocked mercaptosilane and metal halide is conducted in a range of from about 4° to about 100° C. and preferably from about 10° to about 50° C. In addition, the entire process or any step therein, may be conducted at ambient, elevated or reduced pressure.

The entire process of this invention or any step therein, can be conducted in a solvent. Useful solvents can be, for example, any aromatic compound, such as, toluene, benzene, xylene, and any hydrocarbon solvent, such as, hexane, heptane, isooctane and octane.

The following examples are illustrative of the process of this invention.

All operations were performed under a nitrogen atmosphere. Silquest® A-1589 (bis(triethoxysilylpropyl) disulfane), Silquest® A-15304 "more purified disulfide then Silquest® A-1589" (bis(triethoxysilylpropyl) disulfane), Silquest® A-1289 (bis(triethoxysilylpropyl)tetrasufsulfane), toluene, and sodium were used as received without further purification. Deionized water was used as obtained. All GC data is expressed in weight mass % (wt/wt) and obtained from the GC Lab using a Hewlett-Packard 5890 Series II gas chromatograph. The following abbreviations and tradenames (with their descriptions) appear in the examples:

| Abbreviation | Description |
| --- | --- |
| CPTES | Chloropropyltriethoxysilane |
| MPTES | Mercaptopropyltriethoxysilane |
| Blocked Mercaptosilane | 3-(Octanoylthio)-1-propyltriethoxysilane |
| S$_1$-BTESPS | Bis(triethoxysilyl)propyl sulfane |
| S$_2$-BTESPS | Bis(triethoxysilyl)propyldisulfane |
| S$_3$-BTESPS | Bis(triethoxysilyl)propyltrisulfane |
| 2Si | Disiloxane of S-thiocarboxylate mercaptosilane |
| Eluted Heavies | Sum of 2Si and all components that eluted after the 2Si. |
| Solvent® 140 | Mixture of non-aromatic hydrocarbons in the range of C$_{12}$–C$_{14}$ with an average molecular weight of 140 |

COMPARATIVE EXAMPLE 1

At ambient temperature 515.20 g of toluene was treated with 25.00 g of sodium (1.076 moles) and warmed to ~105° C. The molten sodium-toluene suspension was treated with 265.21 g of MPTES (1.079 moles) over the course of 30 minutes resulting in the evolution of hydrogen. After the MPTES addition was completed, the resulting clear, colorless solution was cooled to ~45° C. and treated with 164.75 g of octanoyl chloride (0.982 moles). The addition of octanoyl chloride resulted in an exothermic reaction and the generation of salts. The octanoyl chloride was added over the course of one hour while the reaction temperature slowly increased to 62° C. Once the reaction cooled to 50° C., 215.0 g of deionized water was added resulting in the salts dissolving and the formation of two layers. The aqueous layer was removed, and toluene was removed, in vacuo, recovering 504.72 g of toluene (98% recovery). Recovered was 387.59 g of blocked mercaptosilane as a clear, colorless liquid with the following GC composition (98% efficiency):

| Toluene | Ethyl Octanoate | CPTES | MPTES | Blocked Mercaptosilane | S$_1$-BTESPS | 2Si | Eluted Heavies |
| --- | --- | --- | --- | --- | --- | --- | --- |
| 0.45 | 0.74 | 0.01 | 4.67 | 89.74 | 0.85 | 1.71 | 3.49 |

COMPARATIVE EXAMPLE 2

At ambient temperature, a 50 L reactor was charged with 45.0 lbs of toluene (20.4 kg) followed by the addition of 2.4 lbs of sodium (1015 g, 43.7 moles). This suspension was warmed to ~105° C. and the resulting molten sodium was treated with 24.3 lbs of MPTES (11.0 kg, 44.8 moles) over the course of one hour and 22 minutes resulting in the evolution of hydrogen. After the MPTES addition was completed, the clear solution was cooled to ambient temperature and then treated with 15.5 lbs of octanoyl chloride (7.0 kg, 42.8 moles) over the course of one hour and 35 minutes with the reaction temperature reaching 58° C. The resulting mixture was cooled to 32° C. and then 19.0 lbs of deionized water (8.6 kg) was added resulting in the salts dissolving to give two layers. The aqueous layer was removed, recovering 25.4 lbs of aqueous wastes (11.5 kg) and the toluene was removed in vacuo recovering 46.1 lbs of toluene (20.9 kg, 102% recovery). The product was filtered through a Kuno filter using a 5 micron filter pad, recovering 31.0 lbs of blocked mercaptosilane (14.0 kg) as a clear, yellow liquid with the following GC analysis (85% efficiency):

| Toluene | Ethyl Octanoate | CPTES | MPTES | Blocked Mercaptosilane | S$_1$-BTESPS | 2Si | Eluted Heavies |
| --- | --- | --- | --- | --- | --- | --- | --- |
| 0.69 | 3.80 | 0.01 | 6.40 | 82.04 | 0.71 | 2.28 | 2.97 |

EXAMPLE 1

At ambient temperature, 526.82 g of toluene was treated with 29.28 g of sodium (1.261 moles) and warmed to 110° C. The molten sodium-toluene suspension was treated with 299.15 g of Silquest® A-1589 (0.590 moles) over the course of 45 minutes. The Silquest® A-1589 addition was exothermic and a dark red-purple, opaque solution formed. After the Silqueste® A-1589 addition was completed, the reaction mixture was cooled to ~45° C. and 189.26 g of octanoyl chloride (1.152 moles) was added over the course of one hour resulting in a viscous salt suspension with the reaction reaching 60° C. At ~45° C., the reaction was treated with 278.42 g of water resulting in the salts dissolving to give a clear, yellow-orange toluene layer and a dark, opaque aqueous layer which was removed. 382.62 g of aqueous waste was recovered. The toluene was stripped in vacuo recovering 576.93 g of toluene (106% recovery, contained water). 373.53 g of blocked mercaptosilane was recovered as a clear, dark orange liquid with the following GC analysis (87% efficiency):

| Toluene | Ethyl Octanoate | CPTES | MPTES | Blocked Mercaptosilane | $S_1$-BTESPS | $S_2$-BTESPS | $S_3$-BTESPS | 2Si | Eluted Heavies |
|---|---|---|---|---|---|---|---|---|---|
| 1.41 | 0.76 | 0.01 | 0.43 | 80.36 | 6.80 | 4.97 | 0.01 | 2.90 | 4.06 |

EXAMPLE 2

At ambient temperature, a 50 L reactor was charged with 46.0 lbs of toluene (20.9 kg) followed by the addition of 2.3 lbs of sodium (164 g, 45.8 moles) and warmed to ~110° C. The molten sodium was treated with 22.7 lbs of Silquest® A-1589 (10.3kg) over the course of 69 minutes resulting in an exothermic reaction. After the Silquest® A-1589 addition was completed, the resulting dark suspension was cooled to ~38° C. and then treated with 13.8 lbs of octanoyl chloride (6.3 kg, 38.1 moles) over the course of two hours with the reaction temperature reaching 48° C. The resulting suspension was cooled to ambient temperature and then treated with 22.0 lbs of deionized water (10.0 kg). A 5° C. exotherm was observed and the salts dissolved resulting in two layers. The dark opaque aqueous layer was removed recovering 31.4 lbs of aqueous wastes (14.2 kg). The toluene was stripped recovering 43.9 lbs (19.9 kg, 95% recovery). The product was filtered through a Kuno filter using a 5 micron filter pad recovering 31.0 lbs of blocked mercaptosilane (14.1 kg) as a clear, yellow liquid with the following GC analysis (92% efficiency):

| Toluene | Ethyl Octanoate | CPTES | MPTES | Blocked Mercaptosilane | $S_1$-BTESPS | $S_2$-BTESPS | $S_3$-BTESPS | 2Si | Eluted Heavies |
|---|---|---|---|---|---|---|---|---|---|
| 0.04 | 0.46 | 0.01 | 0.15 | 84.47 | 2.15 | 5.41 | 1.52 | 3.02 | 4.91 |

EXAMPLE 3

At ambient temperature, 509.88 g of toluene was treated with 30.04 g of sodium, (1.299 moles) and warmed to ~110° C. The molten sodium-toluene suspension was treated with 300.97 g of Silquest® Y-15304 (0.590 moles) over the course of 45 minutes. The Silquest® Y-15304 addition was exothermic and a dark red-purple, opaque solution formed. After the Silquest® Y-15304 addition was completed, the reaction mixture was cooled to ~45° C. and 196.01 g of octanoyl chloride (1.169 moles) was added over the course of one hour resulting in a viscous salt suspension with the reaction reaching 60° C. ~At 45° C., the reaction was treated with 270.72 g of water resulting in the salts dissolving to give a clear, yellow-orange toluene layer and a dark, opaque aqueous layer which was removed. 330.89 g of aqueous waste was recovered. The toluene was stripped in vacuo recovering 382.98 g of toluene (75% recovery). 433.06 g of blocked mercaptosilane was recovered as a clear, dark yellow liquid with the following GC analysis (95% efficiency):

EXAMPLE 4

At ambient temperature, a 50 L reactor was charged with 45.0 lbs of toluene (20.4 kg) and 2.34 lbs of sodium (1061 g, 45.7 moles) and warmed to 110° C. The molten sodium was treated with 22.8 lbs of Silquest® Y-15304 (10.3 kg) over the course of 69 minutes resulting in an exothermic reaction. After the Silquest® Y-15304 addition was completed, the resulting dark opaque suspension was cooled to 35° C. and 13.6 lbs of octanoyl chloride (6.2 kg, 37.6 moles) was added over the course of one hour and 49 minutes resulting in an exothermic reaction with the reaction temperature reaching ~50° C. After the octanoyl chloride addition was completed, the resulting suspension was

| Toluene | Ethyl Octanoate | CPTES | MPTES | Blocked Mercaptosilane | $S_1$-BTESPS | $S_2$-BTESPS | $S_3$-BTESPS | 2Si | Eluted Heavies |
|---|---|---|---|---|---|---|---|---|---|
| 0.80 | 0.99 | 0.01 | 1.00 | 79.01 | 7.08 | 5.72 | 0.16 | 2.36 | 4.02 | treated with 22.2 lbs of deionized water (10.1 kg) resulting in the salts dissolving to give two layers. The resulting dark aqueous layer was removed recovering 30.3 lbs (13.7 kg). The toluene was removed in vacuo recovering 45.7 lbs (20.7 kg, 102% recovery). The product was filtered through a Kuno filter using a 5 micron filter pad recovering 30.6 lbs of blocked mercaptosilane (13.9 kg) as a clear, dark yellow liquid with the following GC analysis (92% efficiency):

group consisting of bis[(triethoxysilyl)propyl]polysulfane, bis[(methyldiethoxysilyl)propyl]polysulfane, bis[(triethoxysilyl)isobutyl]polysulfane, bis[(methyldiethoxysilyl)isobutyl]polysulfane, bis[(trimethoxysilyl)propyl]polysulfane, bis[(methyldimethoxysilyl)propyl]polysulfane, bis[(trimethoxysilyl)isobutyl]polysulfane, and bis[(methyldimethoxysilyl)isobutyl]polysulfane.

| Toluene | Ethyl Octanoate | CPTES | MPTES | Blocked Mercaptosilane | S$_1$-BTESPS | S$_2$-BTESPS | S$_3$-BTESPS | 2Si | Eluted Heavies |
|---|---|---|---|---|---|---|---|---|---|
| 0.61 | 0.82 | 0.01 | 2.72 | 82.04 | 2.57 | 6.57 | 0.14 | 2.38 | 3.37 |

EXAMPLE 5

At ambient temperature, 160 g of Solvent® 140 was treated with 11 g of sodium (0.478 moles) and warmed to ~110° C. The molten sodium-Solvent® 140 suspension was treated with 63 g of Silquest® A-1289 (0.117 moles) over the course of 45 minutes. The Silquest® A-1289 addition was exothermic and a dark red-purple, opaque solution formed. After the Silquest® A-1289 addition was completed, the reaction mixture was cooled to ~45° C. and 76 g of octanoyl chloride (0.468 moles) was added over the course of one hour resulting in a viscous salt suspension with the reaction temperature reaching 104° C. At ~45° C., the reaction was treated with 175 g of water resulting in the salts dissolving to give a clear yellow-orange Solvent® 140 layer and a dark, opaque aqueous later which was removed. 236 g of aqueous waste was recovered. The toluene was stripped in vacuo recovering 155 g of Solvent® 140 (97% recovery). 110 g of blocked mercaptosilane was recovered as a clear, dark yellow liquid with the following GC analysis (89% efficiency):

3. The process of claim 1, wherein the alkali metal, alkaline earth metal, and the basic derivatives of alkali metal or alkaline earth metal are selected from the group consisting of lithium, sodium, potassium, magnesium, calcium, lithium hydride, sodium hydride, potassium hydride, magnesium hydride, calcium hydride and mixtures thereof.

4. The process of claim 1, wherein the acyl halide or carbonyl dihalide is of the general formula:

$$R^2C(O)X$$

wherein $R^2$ is halogen or alkyl, alkenyl, aryl, alkaryl or aralkyl of up to about 18 carbon atoms and X is halogen.

5. The process of claim 4, wherein the acyl halide is acetyl chloride, propanoyl chloride, butanoyl chloride, pentanoyl chloride, hexanoyl chloride, heptanoyl chloride, octanoyl chloride 2-ethylhexanoyl chloride, lauroyl chloride, oleoyl chloride, octyl chloroformate, adipoyl chloride, phenylacetyl chloride, benzoyl chloride, terephthaloyl chloride, and phenyl chloroformate.

6. The process of claim 4, wherein the carbonyl dihalide is phosgene, diphosgene, triphosgene, thiophosgene, and oxalyl chloride.

| Toluene | Ethyl Octanoate | CPTES | MPTES | Blocked Mercaptosilane | S$_1$-BTESPS | S$_2$-BTESPS | S$_3$-BTESPS | 2Si | Eluted Heavies |
|---|---|---|---|---|---|---|---|---|---|
| 0.70 | 2.20 | 0.01 | 2.66 | 64.75 | 0.90 | 23.31 | 2.18 | — | — |

What is claimed is:

1. A process for the manufacture of a blocked mercaptosilane comprising:
    reacting at least one polysulfane-containing organosilicon compound of the general formula:

$$(R^1{}_3SiG)_2S_n$$

(a) in which each $R^1$ is independently methoxy, ethoxy or alkyl of from 1 to about 6 carbon atoms, provided, that at least one $R^1$ group is methoxy or ethoxy, G is an alkylene group of from 1 to about 12 carbon atoms and n is from 2 to about 8, with at least one alkali metal, alkaline earth metal or a basic derivative of an alkali metal or alkaline earth metal to provide the corresponding metal salt of the polysulfane-containing organosilicon compound and;
    (b) reacting the metal salt of the polysulfane-containing organosilicon compound with an acyl halide or carbonyl dihalide to provide a blocked mercaptosilane.

2. The process of claim 1, wherein the polysulfane-containing organosilicone compound is selected from the 7. The process of claim 4, wherein the blocked mercaptosilane product is of the general formula:

$$R^2C(O)SGSiR^1{}_3$$

wherein $R^1$, $R^2$, and G have the aforesaid meanings.

8. The process of claim 7, wherein the blocked mercaptosilane product is selected from the group consisting of 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate;

2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate; 3-triethoxysilyl-1-propyl thiopalmitate; 3-triethoxysilyl-1-propyl thiooctanoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; and 2-methyldiacetoxysilyl-1-ethyl thioacetate.

9. The process of claim 1, wherein the range of mole equivalents of alkali metal, alkaline earth metal, basic derivative of alkali metal or alkaline earth metal to polysulfane-containing organosilicon compound is from about 1:1 to about 10:1, and preferably from 2:1 to 2.5:1.

10. The process of claim 1, wherein the range of polysulfane-containing organosilicon compound metal salt to acyl halide is from about 1.25:1 to about 1:1 mole equivalents or carbonyl dihalide is from about 2.25:1 to about 2:1 mole equivalents.

11. The process of claim 1, wherein the reaction between the polysulfane-containing organosilicon compound and the alkali metal, alkaline earth metal, or a basic derivative of alkali metal or alkaline earth metal is conducted at a temperature at which the metal or metal derivative is in the liquid state.

12. The process of claim 1, wherein the reaction of the polysulfane-containing organosilicon compound metal salt and the acyl halide or carbonyl dihalide is conducted at a temperature of from about 10° to about 50° C.

13. The process of claim 1 conducted in a solvent.

14. The process of claim 13, wherein the solvent is selected from the group consisting of toluene, benzene, xylene, hexane, heptane, isooctane and octane.

* * * * *